United States Patent [19]

Kristen et al.

[11] Patent Number: 4,954,347
[45] Date of Patent: Sep. 4, 1990

[54] LONG LASTING COMPOSITION OF PROPAFENONE AND QUINIDINE FOR TREATMENT OF CARDIAC CONDITIONS

[75] Inventors: Edward B. Kristen, Nutley, N.J.; Juan R. Guerrero, Durham, N.C.

[73] Assignee: BASF K & F Corp., Whippany, N.J.

[21] Appl. No.: 189,544

[22] Filed: May 3, 1988

[51] Int. Cl.$^5$ .............................................. A61K 9/20
[52] U.S. Cl. ................................... 424/456; 424/464
[58] Field of Search ................ 424/456, 459, 474, 475

[56] References Cited

U.S. PATENT DOCUMENTS

| | | | |
|---|---|---|---|
| 4,460,605 | 7/1984 | Petrik et al. | 514/651 |
| 4,557,934 | 10/1985 | Cooper et al. | 514/223.5 |
| 4,612,320 | 9/1986 | Franke et al. | 514/327 |

OTHER PUBLICATIONS

Connolly et al., "Clin. Efficacy & Electrophysiology of Oral Propafenone for Vent. Tachycardia", Am. J. Card., vol. 52, pp. 1208–1213, (Dec. 1983).
Siddoway et al., "Polymorphic Oxidative Metabolism of Propafenone in Man", Circulation 68, (Supp. III), p. 64, (Oct. 1983).
Otton et al., "Competitive Inhibition of Sparteine Oxidation in Human Liver . . . ", Life Sciences, vol. 34, pp. 73–80, (1984).
Leeman et al., "Single-Dose Quinidine Treatment Inhibits Metaprolol Oxidation in Extensive Metabolizers", Eur. J. Clin. Pharmocol., 29:739–741, (1986).
Klein et al., "Enhanced Antiarrhythmic Efficacy of Propafenone When Used in Combination with Procainamide or Quinidine", Am. Heart J., (Sep. 1987), pp. 551–558.

Primary Examiner—Thurman K. Page
Assistant Examiner—Leon R. Horne
Attorney, Agent, or Firm—Kenyon & Kenyon

[57] ABSTRACT

A pharmaceutical composition for the treatment of cardiac arrhythmia comprising an effective amount of propafenone in combination with a subtherapeutic amount of quinidine, such that the quinidine potentiates the elimination half-life of the propafenone.

The invention also comprises a method for treating patients with cardiac arrhythmia by means of administering said pharmaceutical composition.

13 Claims, 6 Drawing Sheets

PPF = PROPAFENONE PLASMA LEVELS (ng/mL) DURING PROPAFENONE ADMINISTRATION
PPFQ = PROPAFENONE PLASMA LEVELS (ng/mL) DURING CO-ADMINISTRATION OF PROPAFENONE PLUS QUINIDINE FOR ONE DOSING INTERVAL (8 HOURS)

FIG. 1

PPF = PROPAFENONE PLASMA LEVELS (ng/mL) DURING PROPAFENONE ADMINISTRATION
PPFQ = PROPAFENONE PLASMA LEVELS (ng/mL) DURING CO-ADMINISTRATION OF PROPAFENONE PLUS QUINIDINE FOR ONE DOSING INTERVAL (8 HOURS)

FIG. 2

PROPAFENONE PLASMA CONCENTRATIONS

| | HOURS | PPF | PPFQ |
|---|---|---|---|
| 1 | 0 | 709 | 929 |
| 2 | .5 | 648 | 990 |
| 3 | 1 | 819 | 1314 |
| 4 | 1.5 | 960 | 1577 |
| 5 | 2 | 1020 | 1656 |
| 6 | 2.5 | 1020 | 1582 |
| 7 | 3 | 953 | 1540 |
| 8 | 4 | 1020 | 1491 |
| 9 | 6 | 672 | 1253 |
| 10 | 8 | 471 | 960 |

PPF = PROPAFENONE PLASMA LEVELS (ng/mL) DURING PROPAFENONE ADMINISTRATION
PPFQ = PROPAFENONE PLASMA LEVELS (ng/mL) DURING CO-ADMINISTRATION OF PROPAFENONE PLUS QUINIDINE FOR ONE DOSING INTERVAL (8 HOURS)

FIG. 4

| 5-HYDROXYPROPAFENONE PLASMA CONCENTRATIONS | | |
|---|---|---|
| HOURS | 50HP | 50HPQ |
| 0 | 126 | 92 |
| .5 | 122 | 92 |
| 1 | 131 | 105 |
| 1.5 | 122 | 101 |
| 2 | 126 | 101 |
| 2.5 | 126 | 92 |
| 3 | 147 | 92 |
| 4 | 160 | 109 |
| 6 | 156 | 122 |
| 8 | 118 | 118 |

50HP = 5-HYDROXYPROPAFENONE PLASMA LEVELS (ng/mL) DURING PROPAFENONE ADMINISTRATION

50HPQ = 5-HYDROXYPROPAFENONE PLASMA LEVELS (ng/mL) DURING CO-ADMINISTRATION OF PROPAFENONE PLUS QUINIDINE FOR ONE DOSING INTERVAL (8 HOURS)

FIG. 6

N-DEPROPYLPROPAFENONE PLASMA CONCENTRATIONS

| | HOURS | NDPP | NDPPQ |
|---|---|---|---|
| 1 | 0 | 134 | 146 |
| 2 | .5 | 122 | 146 |
| 3 | 1 | 134 | 187 |
| 4 | 1.5 | 140 | 201 |
| 5 | 2 | 152 | 213 |
| 6 | 2.5 | 155 | 195 |
| 7 | 3 | 180 | 198 |
| 8 | 4 | 180 | 195 |
| 9 | 6 | 161 | 213 |
| 10 | 8 | 128 | 173 |

NDPP = N-DEPROPYLPROPAFENONE PLASMA LEVELS (ng/mL) DURING PROPAFENONE ADMINISTRATION

NDPPQ = N-DEPROPYLPROPAFENONE PLASMA LEVELS (ng/mL) DURING CO-ADMINISTRATION OF PROPAFENONE PLUS QUINIDINE FOR ONE DOSING INTERVAL (8 HOURS)

LONG LASTING COMPOSITION OF PROPAFENONE AND QUINIDINE FOR TREATMENT OF CARDIAC CONDITIONS

Field of the Invention

This invention is concerned with a pharmaceutical composition used in the treatment of cardiac arrhythmia. In particular, the invention relates to a pharmaceutical composition using the antiarrhythmic drug propafenone, in combination with other substances, such that the oxidative metabolism of propafenone in the liver is inhibited. The invention is also concerned with a method for administering such a pharmaceutical composition.

BACKGROUND

Cardiac arrhythmias are disorders involving the electrical impulse generating system of the heart. The disorders include premature contractions (extrasystoles) originating in abnormal foci in atria or ventricles, paroxysmal supraventricular tachycardia, atrial flutter, atrial fibrillation, ventricular fibrillation, and ventricular tachycardia. For further discussion, see, for example, C. S. Goodman and A. Gillman, eds. *The Pharmacological Basis of Therapeutics;* Sixth Edition, New York: Macmillan Publishing Co., 1980; pp. 761–767.

One means of treating cardiac arrhythmia is with the drug propafenone. Propafenone has been shown to be effective in suppressing both supraventricular and ventricular arrhythmias. (Michael A. Brodsky and Byron J. Allen. "Ventricular tachycardia in patients with impaired left ventricular function: the role of propafenone." *Clin. Prog. in Electrophysical and Pacing,* 4:546, 1986.) The antiarrhythmic action of propafenone appears to be due to its propensity to depress conduction and prolong the refractory period in myocardium. (Shen, et al., "Electrophysiologic and hemodynamic effects of intravenous propafenone in patients with recurrent ventricular tachycardia" *JACC* 3: 1291–1307, 1984)

Propafenone undergoes oxidative metabolism by hepatic microsomal enzymes. However, from person to person there are marked genetically determined differences in the rate of hepatic propafenone metabolism. About 10% of the U.S. Caucasian population are considered "poor metabolizers" and 90% are considered "extensive metabolizers." Variations between racial groups have also been reported in the distribution of poor and extensive metabolizers.

Extensive metabolizers of propafenone have lower blood levels and experience a shorter duration of effect than poor metabolizers. These extensive metabolizers may require more frequent dosages of higher amounts of propafenone to control their arrhythmia.

Consequently, current formulations of propafenone are metabolized too quickly by many individuals. Also, ideal blood levels may not be reached or may not be maintained for a long enough period of time to provide efficient control of cardiac arrhythmia.

The object of the present invention is to provide a formulation of propafenone and a means of administering this formulation which modulates propafenone oxidative metabolism. Other objectives are to decrease interindividual variations of propafenone metabolism; to uniformly raise blood levels among the total population taking propafenone; and to increase the duration of effect among these individuals. Achievement of these objectives would result in increased intervals between administration, improved medical management of patients with cardiac arrhythmia, and greater success in the treatment of this condition.

SUMMARY OF THE INVENTION

These and other objects are achieved by the present invention which relates to a pharmaceutical composition suitable for the treatment of a patient having cardiac arrhythmia. The composition comprises, in unit dosage form, an effective amount of propafenone in combination with a subtherapeutic amount of quinidine, such that the quinidine prolongs the elimination half-life of the propafenone in the same formulation. The bioavailability of propafenone will also increase during concomitant administration of propafenone plus quinidine so less propafenone is metabolized and more reaches the systemic circulation. Such a composition may be in the form of a tablet, capsule, or caplet, preferably with an enteric coating. A preferred composition comprises from about 50 mg to about 600 mg propafenone hydrochloride and about 25 mg to about 200 mg quinidine such that from about 1 unit dose to about 2 unit doses per day would be administered. An especially preferred composition is formulated from about 300 mg propafenone and about 100 mg quinidine with the remainder being either a pharmaceutical carrier such as lactose sugar, gum binder, and an inert polymeric extender which is calculated to provide about a 5 to 10 grain tablet, capsule, or caplet.

The invention as well relates to a method for treating patients with cardiac arrhythmia which comprises orally administering to a patient, at unit dosage levels, therapeutic amounts of propafenone in combination with subtherapeutic amounts of quinidine such that the quinidine potentiates the elimination half-life of propafenone.

DETAILED DESCRIPTION OF THE INVENTION

Propafenone is an antiarrhythmic drug available for oral and intravenous administration. The structural formula and chemical name for propafenone is:

HYDROXY-METHOXY METABOLITES

2'-[3-(prophylamino)-2-(hydroxy)-(propoxy)-3-phenyl-propiophenone hydrochloride
   Molecular formula: $C_{21}H_{27}NO_3 \cdot HCl$
   Molecular weight: 377.92

Propafenone blocks fast inward sodium channels. It is also a weak beta-blocker with weak calcium antagonist activity. It is effective against recurrent supraventricular and ventricular arrhythmias, premature ventricular contractions, and ventricular tachycardia.

Propafenone can be successfully utilized in both the short-term and long-term treatment of arrhythmia. Administered intravenously, it is an effective treatment for ventricular arrhythmias, and supraventricular arrhythmias. Oral propafenone is an effective agent in the management of premature ventricular complexes and chronic recurrent supraventricular tachycardia. It does not appear to cause significant hemodynamic changes or life-threatening toxic side effects.

Propafenone is extensively metabolized in the liver, where it undergoes oxidative metabolism to form 5-hydroxy and hydroxy-methoxy metabolites.

The oxidation of propafenone appears to occur at the site of the hepatic microsomal mono-oxygenase cytochrome P450. Other substances which are oxidized by cytochrome P450 isozymes include debrisoquin, sparteine, and metoprolol.

The pharmcokinetic and pharmacodynamic characteristics of propafenone are striking in their great interindividual variability. Some individuals can be considered "extensive propafenone metabolizers," characterized by a relatively short elimination half-life, low plasma concentration, high oral clearance, disproportionate dose-concentration relationship, and detectable quantities of the metabolite 5-hydroxypropafenone. Others are "poor propafenone metabolizers," characterized by a long elimination half-life, high plasma concentration, low oral clearance, proportionate dose-concentration relationship, and absence of detectable 5-hydroxypropafenone. (Siddoway, et al. "Polymorphic oxidative metabolism of propafenone in man," Circ. 68;64, 1987.)

Approximately 90% of the American population are extensive metabolizers of propafenone, while only 10% are poor metabolizers. This invention is intended to provide an improved formulation and means of administration of propafenone for the vast majority of individuals who are extensive metabolizers.

Quinidine is the isomer of quinine, found naturally in cinchona bark. The structural formula of quinidine is:

Quinidine is a class I antiarrhytmic drug. It is generally regarded as a myocardial depressant. It depresses cardiac irritability, conduction velocity, and contractility. In experimental animals, quinidine has been shown to raise the threshold for electrically induced arrhythmias, prevent or terminate the "late" ventricular tachycardias following coronary artery occlusion, and terminate or prevent circus-movement flutter. The major clinical uses of quinidine are for the prevention and abolition of certain cardiac arrhythmias. These would include ventricular tachycardia, atrial flutter, atrial fibrillation, and premature systole.

Quinidine has been shown to inhibit the oxidation of certain drugs which are believed to be metabolized via the P450 cytochrome system. For example, the in vitro oxidation of sparteine has been shown to be markedly inhibited in combination with quinidine. This is thought to be due to competition with the catalytic enzyme site(s) that oxidize sparteine.

Another in vivo study measured the effect of quinidine on the oxidative metabolism of metoprolol. Two hours after ingestion of 50 mg. of quinidine sulfate, 100 mg. of metoprolol was administered. Under this regimen the single dose of quinidine in extensive metabolizers produced a threefold increase of total metoprolol and the active (−) metoprolol isomer plasma concentration.

The oxidized metabolite of metoprolol is alpha-hydroxymetoprolol. The oxidized metabolite of propafenone is 5-hydroxypropafenone. These oxidation products are significantly different. In the case of metoprolol, oxidation occurs on the aliphatic alpha carbon, whereas in the case of propafenone, oxidation occurs on C-5 of an aromatic ring. The inhibition of propafenone metabolism by quinidine, therefore, would not be expected based on the effect of quinidine metabolism on metoprolol.

Furthermore, the drugs are structurally different, with unique physical and pharmacological properties. The half-life of metoprolol is approximately 3 to 7 hours. The half-life of propafenone is between two and 30 hours. Metoprolol is primarily a beta-adrenergic blocking agent. Propafenone is only a weak beta-blocker. Its primary electrophysiological effect is the blockade of the fast sodium channel of cardiac cells. The two drugs also have significantly different levels of bioavilability. Systemic bioavilability of metoprolol is 40–50%, whereas systemic bioavilability of propafenone is only 5–12%.

As described in greater detail below, it was surprising to find therefore that when a pharmaceutical composition of the present invention was administered to a patient, the oxidative metabolism of propafenone was modulated, causing the maximum plasma concentration, elimination half-life, and steady state levels of plasma propafenone to be increased.

The invention also discloses that a means of administering this pharmaceutical composition also improved treatment efficiency, safety, and patient compliance.

The components of the present invention can be formulated into a tablet, capsule, caplet, suspension or liquid, administered orally. The effective dose of the present invention is the amount required to successfully treat cardiac arrhythmia, and is readily ascertainable by one skilled in the art. Propafenone hydrochloride is administered in doses from 450 mg/day (150 mg every 8 hours) to 900 mg/day (300 mg every 8 hours). Quinidine gluconate is administered in 325 mg tablets either two or three times daily.

For oral administration, the pharmaceutical composition in the form of a tablet, capsule, or caplet is preferably made in the form of a dosage unit containing a particular amount of the active ingredients. The tablet, capsule, or caplet is made by combining the compounds of the present invention with excipients such as sodium citrate, calcium carbonate, and dicalcium phosphate, disintegrants such as starch, alginic acid, and certain complex silicates, together with binding agents such as polyvinylpyrrolidone, gelatin and acacia. Lubricating agents such as magnesium stearate, sodium lauryl sulfate, and talc are often very useful for tabletting purposes. Solid compositions of a similar type may also be employed as fillers in soft and hard-filled gelatin capsules. Preferred materials would include lactose as well as high molecular weight polyethylene glycols. The tablet, capsule, or caplet is then formed according to means known to one of ordinary skill in the art.

The invention also includes a tablet, capsule, or caplet with an enteric coating. This is an acid-resistant film that renders the tablet, capsule, or caplet resistant to dissolution by gastric juice. The enteric-coating process is carried out by dissolving a film-coating material which is resistant to gastric dissolution in a volatile solvent. This solution is then sprayed onto filled tablets, capsules, or caplets.

It is also possible to select a material for the capsule wall that is resistant to gastric dissolution but capable of dissolution in the intestine. For example, it is possible to select certain types of gelatin that do not dissolve at the pH of the stomach but can dissolve at the pH of the intestine.

Alternatively, the active ingredients may be dissolved in an aqueous medium for oral administration and the appropriate agents added to mask the unpalatable taste of the propafenone and quinidine.

EXAMPLES

Example I

A dry solid pharmaceutical composition is prepared by blending the following materials together in the proportions by weight specified below:
Propafenone: 300
Quinidine: 100
Carboxylic Acid: 50
Sodium Citrate: 25
Alginic Acid: 10
Polyvinylpyrrolidone: 10
Magnesium Stearate: 5

After the dried composition is thoroughly blended, tablets are punched from the resulting mixture, each tablet being of such size that it contains 300 mg. of the active ingredient. Other tablets are also prepared in a similar fashion containing 150 and 225 mg. of the active ingredient, respectively, by using the appropriate amount of the propafenone and quinidine in each case.

EXAMPLE II

A dry solid pharmaceutical composition is prepared by combining the following materials together in the proportions by weight indicated below:

Propafenone: 300
Quinidine: 100
Carboxylic Acid: 50
Calcium Carbonate: 20
Polyethylene glycol, average: molecular weight 4000: 30

The dried solid mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 200-550 mg. of the active ingredients.

EXAMPLE III

A pharmacokinetic evaluation of the interaction between quinidine and propafenone hydrochloride was conducted. Subjects were males and females over age 21 with a history of clinically significant ventricular arrhythmial defined as Lown Grade 2 (>30 PVCs/hr.) or higher. Only patients requiring propafenone therapy were evaluated. An open-label design was used.

In Phase I of the study, patients on a q8 hr. dosage regimen had their optimal dosage continued every eight hours for at least four days, at which time, plasma propafenone levels were measured for one eight hour dosing interval. Immediately following Phase I, patients were administered 80 mg. quinidine gluconate every eight hours concomitantly with their dose of propafenone. After at least four days of concomitant administration, plasma propafenone levels were measured for one eight hour dosing interval. All drug doses were administered with about 180 ml. tap water. The last dose of each study phase was administered after a minimum of eight hours fasting following by an additional three hour fasting period. Water was allowed ad lib. Ten ml. blood samples for propafenone assay were obtained at hours 0, 0.5, 1, 1.5, 2, 2.5, 3, 4, 6 and 8. Blood samples for quinidine assay were obtained at hours 0 and 8 ("trough" levels). All blood samples were collected in heparinized tubes. Samples were promptly centrifuged to separate plasma and RBC's, frozen, and stored prior to analysis.

RESULTS

The results from one patient indicate that administration of quinidine concomitantly with propafenone has a very pronounced effect on the blood levels of propafenone. Co-administration of quinidine with propafenone results in propafenone plasma concentrations which are about 150% more than those observed when propafenone is administered alone.

Figure 1:
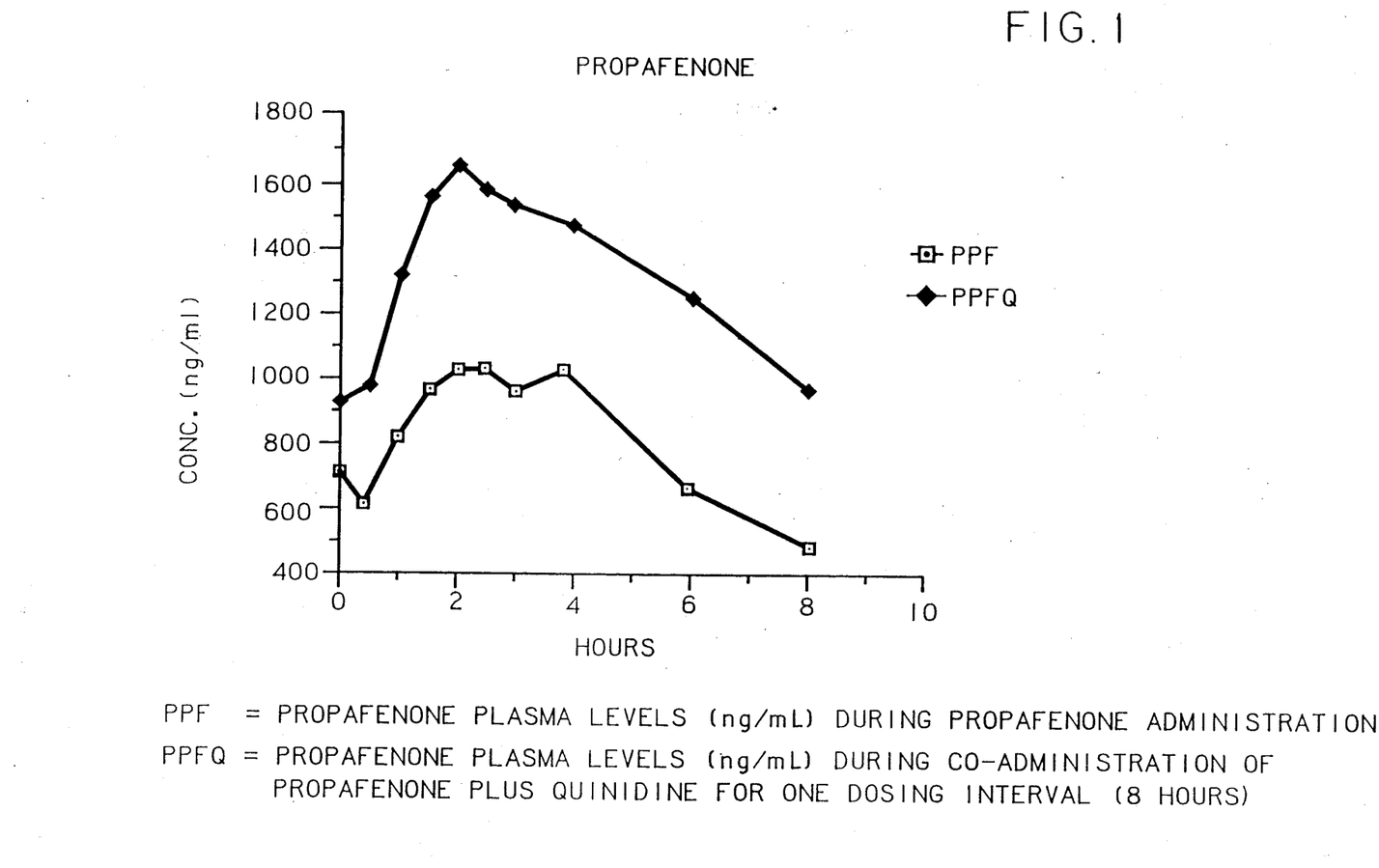
FIG. 1 is a graph of plasma levels of propafenone following administration of the claimed composition compared to administration of a propafenone standard.

FIG. 1 is a graph that compares propafenone plasma levels (ng/mL) during propafenone administration (PPF) and propafenone plasma levels (ng/mL) during co-administration of propafenone plus quinidine for one 8 hour dosing interval (PPFQ).

Figure 2:
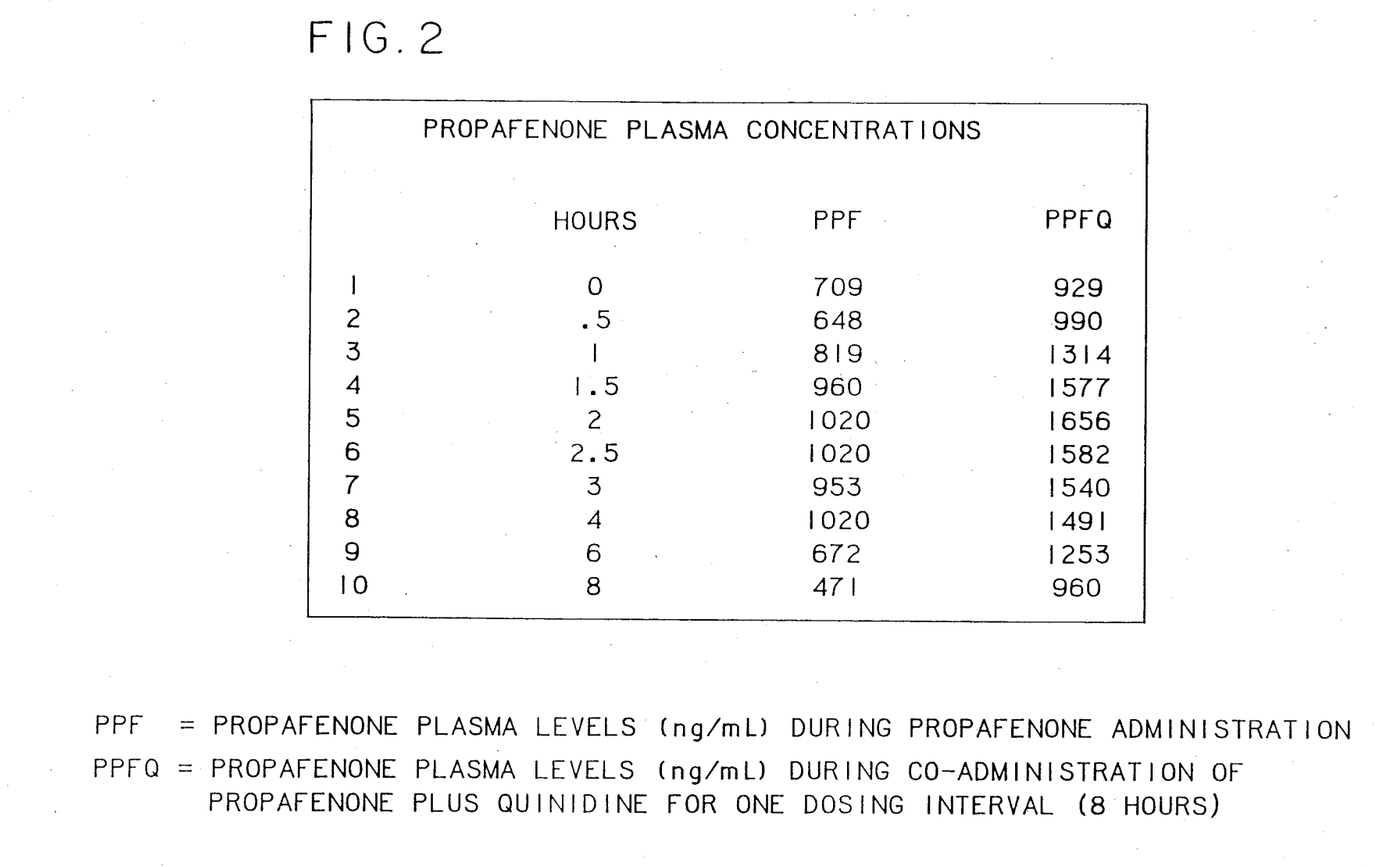
FIG. 2 is a table of the data represented in FIG. 1.

FIG. 2 is a table of the data represented in FIG. 1 that compares propafenone plasma levels (ng/mL) during propafenone administration (PPF) and propafenone plasma levels (ng/mL) during co-administration of propafenone plus quinidine for one 8 hour dosing interval (PPFQ).

Figure 3:
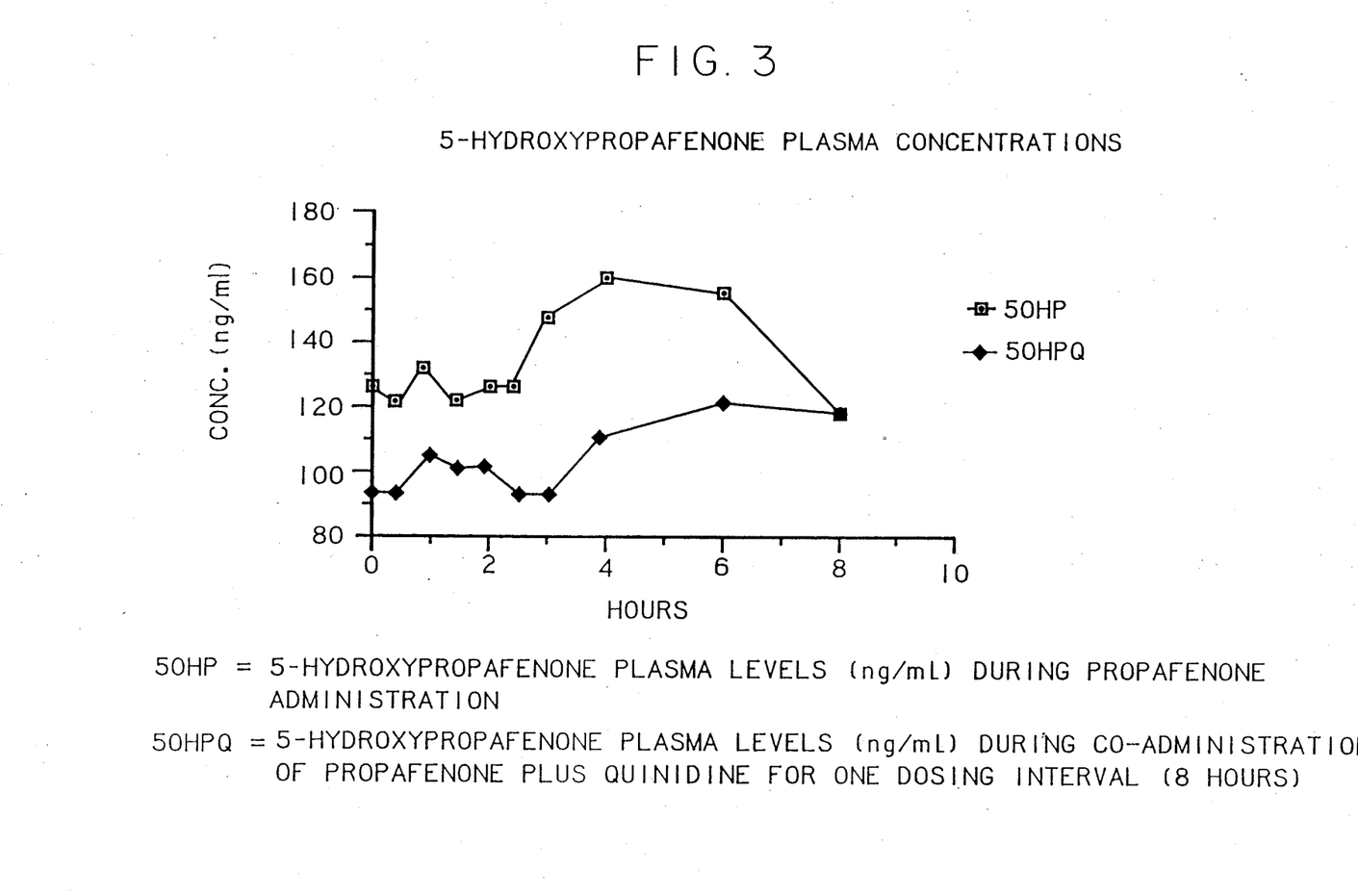
FIG. 3 is a graph of plasma levels of 5-hydroxypropafenone, a metabolite of propafenone, following administration of the chemical composition compared to administration of a propafenone standard.

FIG. 3 is a graph that compares 5-hydroxypropafenone plasma levels (ng/mL) during propafenone administration (5OHP) and 5-hydroxypropafenone plasma levels (ng/mL) during co-administration of propafenone plus quinidine for one 8 hour dosing interval (5OHPQ).

Figure 4:
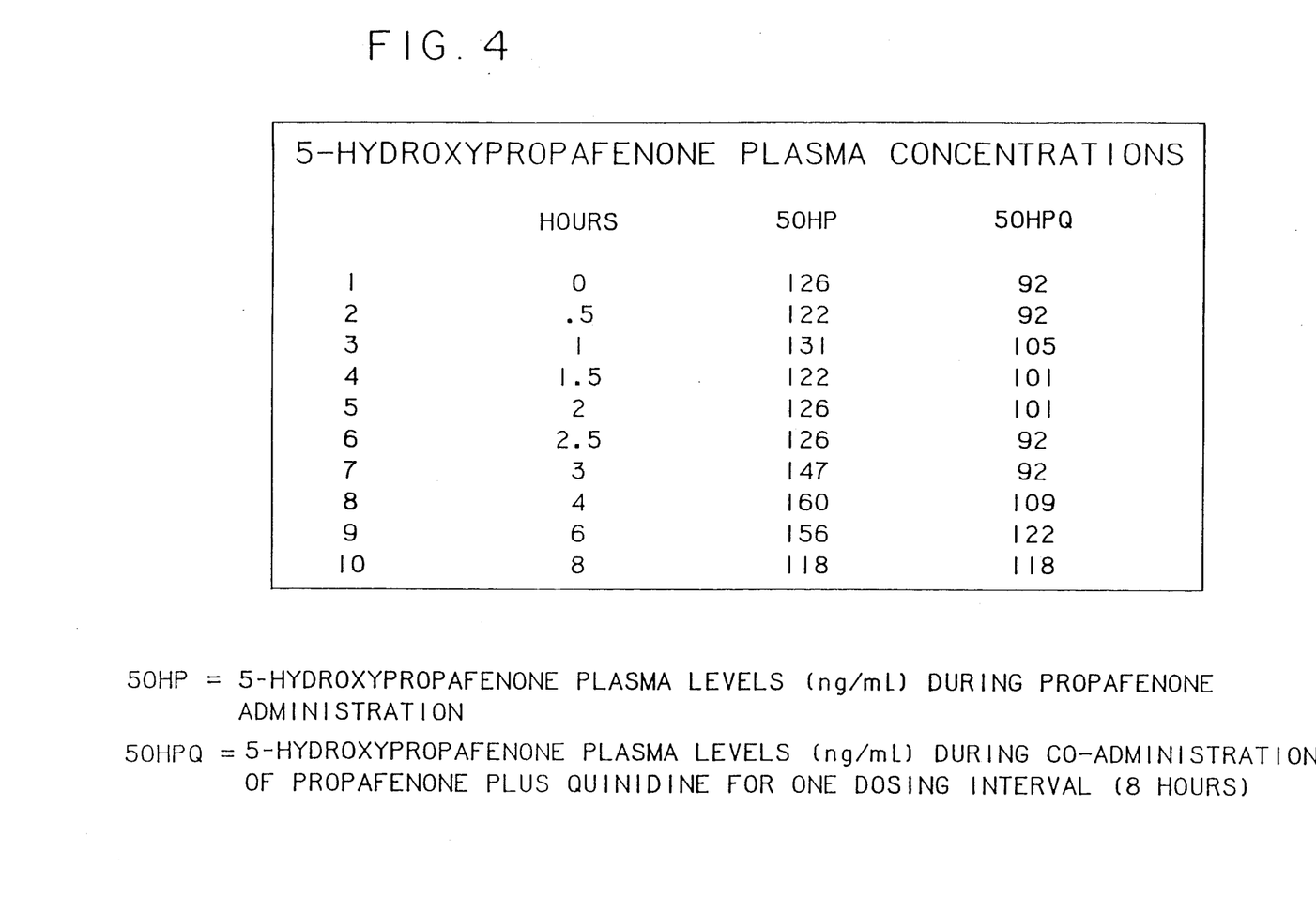
FIG. 4 is a table of the data represented in FIG. 3.

FIG. 4 is a table of the data represented in FIG. 3 that compares 5-hydroxypropafenone plasma levels (ng/mL) during propafenone administration (5OHP) and 5-hydroxypropafenone plasma levels (ng/mL) during co-administration of propafenone plus quinidine for one 8 hour dosing interval (5OHPQ).

Figure 5:
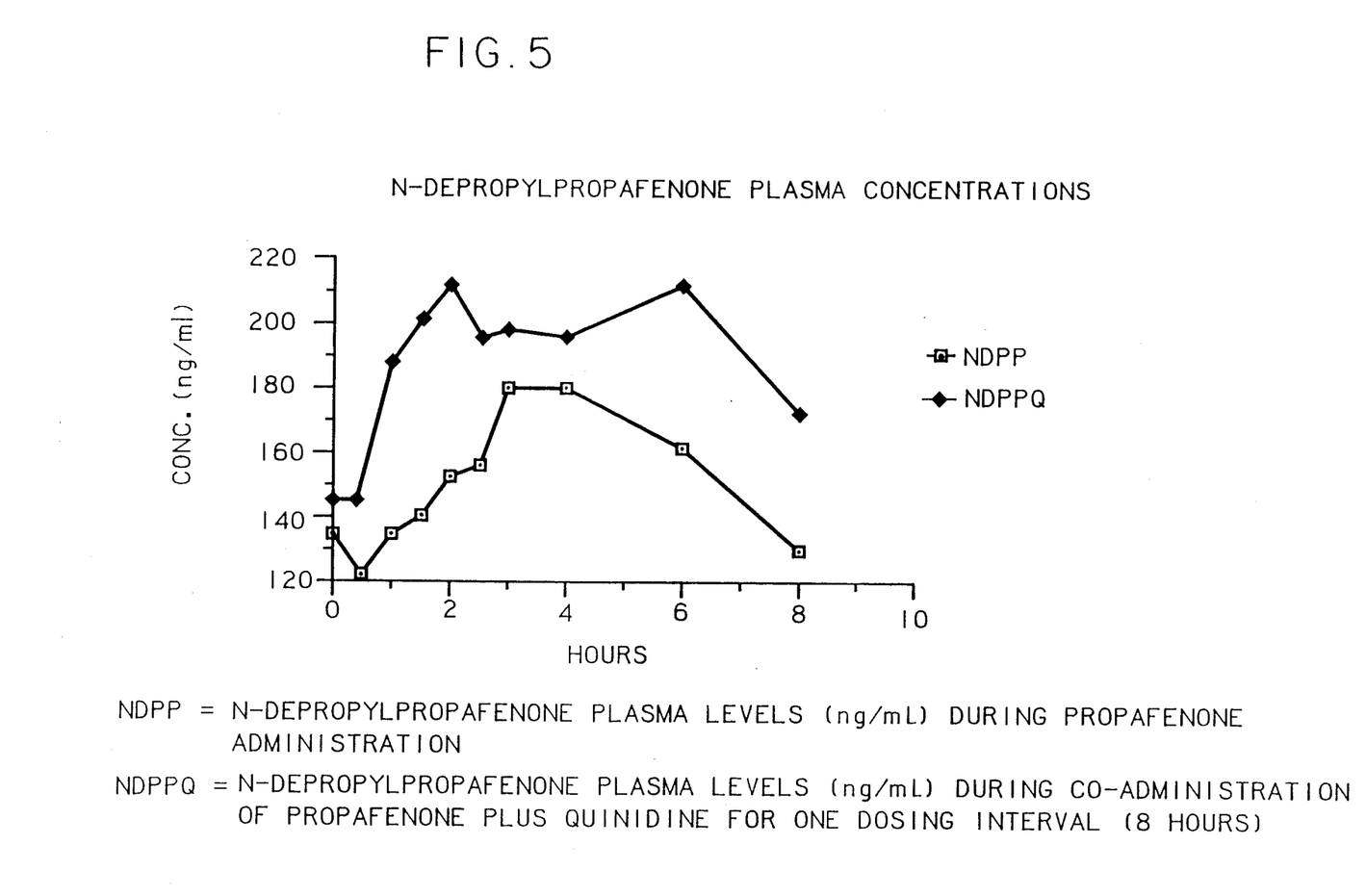
FIG. 5 is a graph of plasma levels of N-depropylpropafenone, a metabolite of propafenone, following administration of the claimed composition compared to administration of a propafenone standard.

FIG. 5 is a graph that compares n-depropylpropafenone plasa levels (ng/mL) during propafenone administration (NDPP) and n-depropylpropafenone plasma levels (ng/mL) during co-administration of propafenone plus quinidine for one 8 hour dosing interval (NDPQ).

Figure 6:
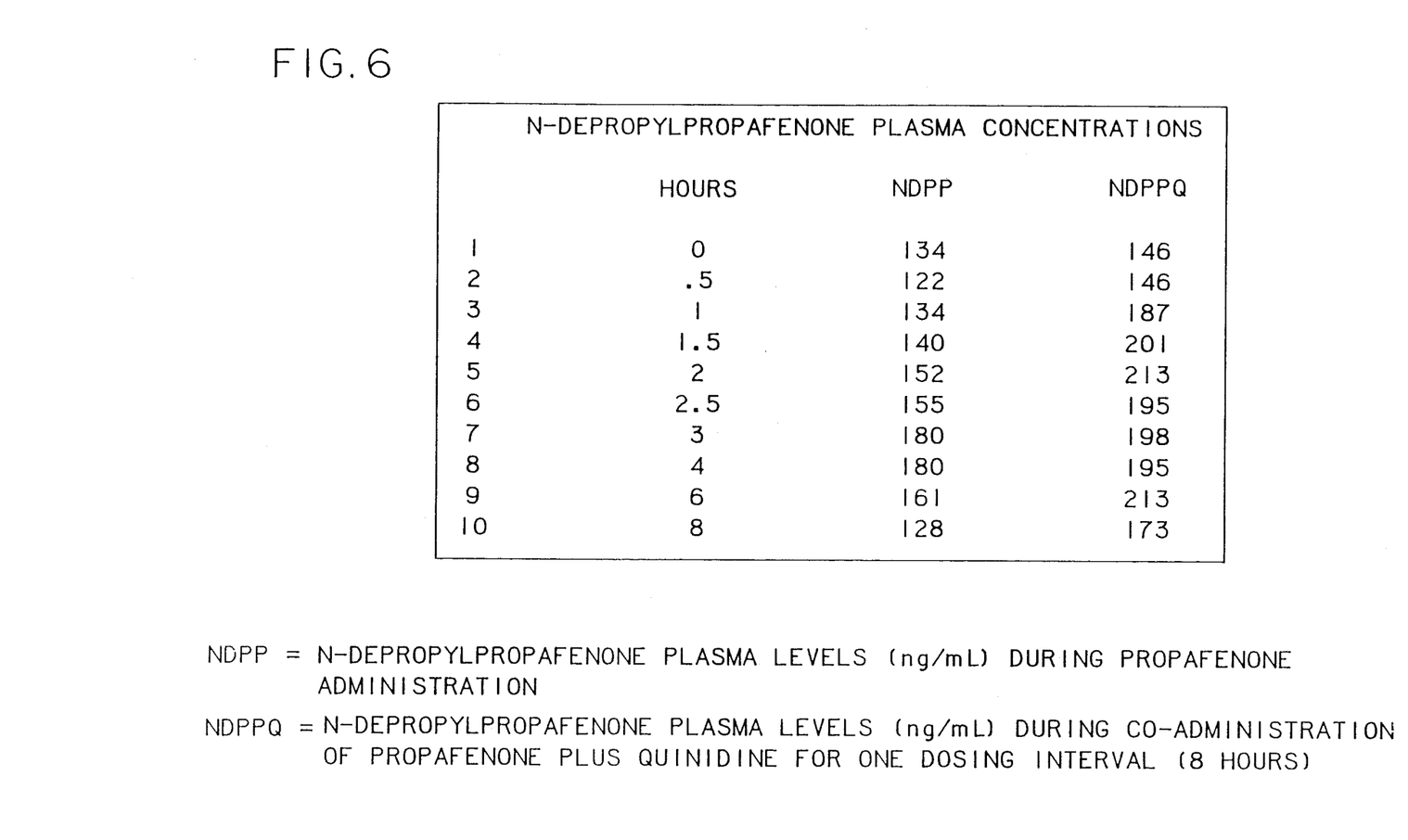
FIG. 6 is a table of the data represented in FIG. 5.

FIG. 6 is a table of the data represented in FIG. 5 that compares n-depropylpropafenone plasma levels (ng/mL)during propafenone administration (NDPP) and n-depropylpropafenone plasma levels (ng/mL) during co-administration of propafenone plus quinidine for one 8 hour dosing interval (NDPQ).

What is claimed is:

1. A pharmaceutical composition suitable for the treatment of a patient having cardiac arrhythmia comprising: an antiarrhythmic therapeutically effective amount of propafenone of 50-600 mg and a subtherapeutic amount of quinidine effective for prolonging the elimination half-life of the propafenone, in combination with a pharmaceutical carrier therefor.

2. A pharmaceutical composition according to claim 1, wherein the quinidine is present in an amount from about 25-200 mg/tablet.

3. A pharmaceutical composition according to claim 1, comprising propafenone in the amount from about 50-600 mg/tablet and quinidine in a subtherapeutic amount from about 25-200 mg/tablet.

4. A pharmaceutical composition according to claim 1 in the form of a tablet, a hard or soft-gelatin capsule, or a suspension or a syrup for oral administration.

5. A pharmaceutical composition according to claim 5, wherein the tablet, capsule, or caplet are coated with an enteric coating.

6. A pharmaceutical composition according to claim 1, wherein the pharmaceutical carrier is selected from a group consisting of a sugar, a starch, a gum, corn syrup, water and mixtures thereof.

7. A pharmaceutical composition according to claim 1, comprising propafenone in the amount from about 50-600 mg/tablet; quinidine in a subtherapeutic amount from about 25-200 mg/tablet; a pharmaceutical carrier selected from a group consisting of a sugar, a starch, a gum, corn syrup and mixtures thereof and wherein said composition is in the form of an enteric coated tablet.

8. A pharmaceutical composition according to claim 1 comprising propafenone in the amount from about 150-900 mg/tablet; quinidine in a subtherapeutic amount from about 25-200 mg/tablet; a pharmaceutical carrier selected from a group consisting of a sugar, a starch, a gum, corn syrup and mixtures thereof and wherein said composition is in the form of an enteric coated tablet for administration once per day.

9. A method of treating cardiac arrhythmia comprising: administering to a patient having cardiac arrhythmia a pharmaceutical composition comprising an antiarrhythmic therapeutic effective amount of propafenone of 50–600 mg and a subtherapeutic amount of quinidine effective for prolonging the elimination half-life of the propafenone in combination with pharmaceutical carriers therefor.

10. A method of treating cardiac arrhythmia according to claim 7, wherein the effective dose is about 50 mg–600 mg dosage unit administered one or two times per 11. A method, of treating cardiac arrhythmia according to claim 7, wherein the effective dose produces minimum blood levels of about 200 ng/ml and maximum blood levels of about 2000 ng/ml of propafenone.

12. A pharmaceutical composition in accordance with claim 1 wherein the composition is in the form of a table.

13. A pharmaceutical carrier comprises starch.

* * * * *